US009650382B2

(12) United States Patent
Ratilainen et al.

(10) Patent No.: US 9,650,382 B2
(45) Date of Patent: May 16, 2017

(54) HETEROARYLAMIDE DERIVATIVES HAVING ANTIANDROGENIC PROPERTIES

(71) Applicant: MEDEIA THERAPEUTICS LTD, Kuopio (FI)

(72) Inventors: Jari Ratilainen, Kulho (FI); Milla Koistinaho, Paukarlahti (FI); Anu Muona, Harjamaki (FI)

(73) Assignee: ARANDA PHARMA LTD, Kuopio (FI)

( * ) Notice: Subject to any disclaimer, the term of this patent is extended or adjusted under 35 U.S.C. 154(b) by 0 days.

(21) Appl. No.: 14/371,927

(22) PCT Filed: Jan. 11, 2013

(86) PCT No.: PCT/FI2013/050027
§ 371 (c)(1),
(2) Date: Jul. 11, 2014

(87) PCT Pub. No.: WO2013/104830
PCT Pub. Date: Jul. 18, 2013

(65) Prior Publication Data
US 2015/0005308 A1    Jan. 1, 2015

(30) Foreign Application Priority Data
Jan. 13, 2012  (FI) ..................................... 20125039

(51) Int. Cl.
| | |
|---|---|
| *A01N 43/58* | (2006.01) |
| *A61K 31/60* | (2006.01) |
| *A61K 31/50* | (2006.01) |
| *A61K 31/495* | (2006.01) |
| *A01N 43/40* | (2006.01) |
| *A61K 31/44* | (2006.01) |
| *C07D 487/00* | (2006.01) |
| *C07D 213/00* | (2006.01) |
| *C07D 211/78* | (2006.01) |
| *C07D 211/90* | (2006.01) |
| *C07D 213/84* | (2006.01) |
| *C07D 487/04* | (2006.01) |
| *C07D 213/30* | (2006.01) |
| *C07D 213/57* | (2006.01) |
| *C07D 213/61* | (2006.01) |
| *A61K 31/435* | (2006.01) |
| *A61K 31/444* | (2006.01) |
| *A61K 31/5025* | (2006.01) |
| *C07D 213/89* | (2006.01) |
| *C07D 401/06* | (2006.01) |

(52) U.S. Cl.
CPC .......... *C07D 487/04* (2013.01); *A61K 31/435* (2013.01); *A61K 31/444* (2013.01); *A61K 31/5025* (2013.01); *C07D 213/30* (2013.01); *C07D 213/57* (2013.01); *C07D 213/61* (2013.01); *C07D 213/89* (2013.01); *C07D 401/06* (2013.01)

(58) Field of Classification Search
USPC .......................... 514/248, 357; 544/236, 239
See application file for complete search history.

(56) References Cited

U.S. PATENT DOCUMENTS

2006/0241180 A1    10/2006  Dalton et al.

FOREIGN PATENT DOCUMENTS

| CN | 1602299 A | 3/2005 |
|---|---|---|
| DE | 102007058747 A1 | 6/2009 |
| EP | 0 100 172 A1 | 2/1984 |
| EP | 1 462 442 A1 | 9/2004 |
| JP | 2009-108081 A | 5/2009 |
| JP | 2014-532686 A | 12/2014 |
| WO | WO 2004/041277 A1 | 5/2004 |
| WO | WO 2008/011072 A2 | 1/2008 |

(Continued)

OTHER PUBLICATIONS

Wolff et. al., "Burger's Medicinal Chemistry and Drug Discovery," 5th Ed. Part 1, pp. 975-977 (1995).*
Banker, et. al., (1996), Modern Pharmaceuticals, p. 596.*
International Search Report and Written Opinion dated Mar. 12, 2013 issued in PCT/FI2013/050027.
English Abstract of WO 2009/0711252 A1, dated Jun. 11, 2009.
Perlmutter, et al., "Androgen Deprivation Therapy in the Treatment of Advanced Prostate Cancer"; Reviews in Urology, New York University School of Medicine, vol. 9, Suppl 1, 2007, pp. 53-58.

(Continued)

*Primary Examiner* — Jeffrey H Murray
*Assistant Examiner* — Oluwafemi Masha
(74) *Attorney, Agent, or Firm* — Scully Scott Murphy and Presser

(57) ABSTRACT

The invention relates to novel heteroarylamide derivatives having formula (I) and N-oxides, stereoisomers and pharmaceutically acceptable salts thereof, where $R_A$, $R_B$, R11, R', R", z and X are as defined in the claims. The arylamide derivatives of formula (I) have antiandrogenic properties. The invention also relates to compounds of formula (I) for use as a medicament and to pharmaceutical compositions comprising them and to their preparation.

21 Claims, No Drawings

(56) References Cited

FOREIGN PATENT DOCUMENTS

| WO | 2009/071252 A1 | 6/2009 |
| WO | WO 2010/116342 A2 | 10/2010 |
| WO | 2013/064681 A1 | 5/2013 |

OTHER PUBLICATIONS

Taplin, Mary-Ellen, "Drug Insight: Role of the Androgen Receptor in the Development and Progression of Prostate Cancer"; Nature Clinical Practice Oncology, vol. 4, No. 4, Apr. 2007, pp. 236-244.
Hara, et al., "Novel Mutations of Androgen Receptor: A Possible Mechanism of Bicalutamide Withdrawal Symptoms"; Cancer Research 63, Jan. 1, 2003, pp. 149-153.
Chen, et al., "Molecular Determinants of Resistance to Antiandrogen Therapy"; Nature Medicine, vol. 10, No. 1, Jan. 2004, pp. 33-39.
Block, et al., In Pursuit of Cyclopropanethione: Cyclopropanethione S-Oxide and S,S-Dioxide; J. Am. Chem. Soc., 1992, 114, p. 3492-3499.
Chinese Office Action and Search Report issued Apr. 13, 2015 in Application No. 201380005365.7 (English Translation Only).
Japanese Office Action dated Aug. 31, 2016 issued in corresponding Japanese Patent Application No. 2014-551659.

\* cited by examiner

HETEROARYLAMIDE DERIVATIVES HAVING ANTIANDROGENIC PROPERTIES

THE FIELD OF THE INVENTION

The present invention relates to new heteroarylamide derivatives, their preparation, pharmaceutical compositions containing them and their use in the treatment of androgen receptor related disorders, such as benign prostate hyperplasia and cancer, particularly prostate cancer and/or castration-resistant prostate cancer.

BACKGROUND OF THE INVENTION

Androgens are produced by testes and adrenal glands and they play a critical role in the development and physiology of normal prostate. The etiology of benign prostate hyperplasia (BPH) and prostatic neoplasia which can progress to adenocarcinoma is androgen-dependent. Treatment of choice for BPH and prostate cancer (PCa) is reduction of androgen action in the prostate. In fact, almost 90% of men between ages 40 to 90 years develop either BPH or PCa. PCa is the second leading cause of cancer-related death and the most frequently diagnosed malignancy in men. PCa remains incurable in metastatic setting. As the incidence of PCa increases with age, the number of newly diagnosed cases rises continuously due to increased life expectancy of the population.

The conventional initial treatment for PCa is hormone or androgen deprivation therapy (ADT). Experimental ADT was first described already in 1941. ADT via surgical castration or by chemical castration using luteinizing hormone releasing hormone agonists is universally accepted first-line therapy in advanced PCa. See Perlmutter M, Lepor H. Androgen deprivation therapy in the treatment of advanced prostate cancer Rev Urol. 2007; 9(Suppl 1): S3-S8 and references therein.

Maximal androgen blockade is achieved by combining ADT with an anti-androgen treatment. Anti-androgens compete with endogenous androgens, testosterone and dihydrotestosterone, for binding in the ligand-binding pocket of the androgen receptor (AR). AR belongs to the superfamily of nuclear hormone receptors and is mainly expressed in reproductive tissues and muscles. Ligand binding to AR promotes its dissociation from heat shock proteins and other chaperones, leading to dimerization of the receptor, phosphorylation and subsequent translocation into the nucleus where AR binds to androgen responsive elements present in the regulatory regions of multiple genes involved in the growth, survival and differentiation of prostate cells.

The first non-steroidal anti-androgen, flutamide was approved for PCa in 1989 and the structurally related compounds, bicalutamide and nilutamide, were launched in 1995 and 1996, respectively. Non-steroidal compounds are more favorable than steroidal anti-androgens in clinical applications because of the lack of cross-reactivity with other steroid receptors and improved oral bioavailability. Of this structural class of propanamide anti-androgens, bicalutamide is the most potent, best tolerated and the leading anti-androgen on the market. Bicalutamide is described in patent literature for example in European patent EP 0100172. Certain arylamide derivatives have also been described in documents WO 2008/011072 A2, WO 2010/116342 and WO 2010/092546 A1 as selective androgen receptor modulators.

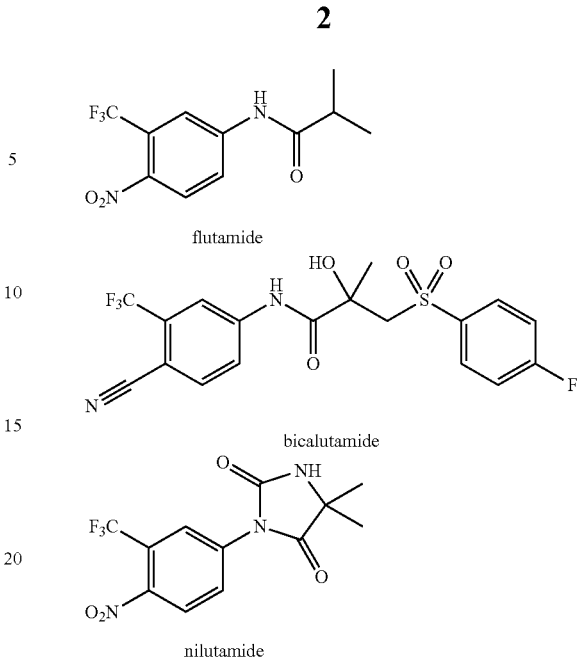

flutamide bicalutamide nilutamide

Unfortunately, although ADT and anti-androgen treatment typically result in early beneficial responses, PCa then progresses to a state where androgen deprivation fails to control the malignancy despite minimal testosterone levels. This state is termed castration-resistant prostate cancer (CRPC) (or hormone-refractory prostate cancer, HRPC) and is the lethal form of the disease. CRPC is believed to emerge after genetic and/or epigenetic changes in the prostate cancer cells and it is characterized by re-activation of the growth of cancer cells that have adapted to the hormone-deprived environment in the prostate.

The growth of cancer cells in CRPC remains dependent on the function of AR and studies over the past decade demonstrate that CRPC cells employ multiple mechanisms to re-activate AR. See Chen C D, Welsbie D S, Tran C, Baek S H, Chen R, Vessella R, Rosenfeld M G, Sawyers C L. Molecular determinants of resistance to antiandrogen therapy. Nat Med 2004 January; 10(1): 33-39 and references therein. The major mechanisms include amplification of AR gene or up-regulation of AR mRNA or protein, point mutations in AR that allow activation of the AR by non-androgenic ligands or even anti-androgens, changes in the expression levels of co-activators and co-repressors of AR transcription, and expression of alternatively spliced and constitutively active variants of the AR. Thus, drugs targeting AR signaling could still be effective in the prevention and treatment of CRPC.

The limited utility of currently available anti-androgens is most likely related to an incomplete AR inhibition under certain circumstances (Taplin M E. Drug insight: role of the androgen receptor in the development and progression of prostate cancer. Nat Clin Pract Oncol. 2007 April; 4(4): 236-244). Multiple molecular mechanisms may contribute to the failure of standard anti-androgen treatments. The use of anti-androgens that target ligand-binding domain of the AR, such as bicalutamide, can lead to selection of prostate cancer cells that harbor point mutations in the ligand-binding domain. In some cases these mutations can cause prostate cancer cells to convert antagonists to agonists. AR mutations are found in 10-40% of metastatic tumors. More than 70 mutations in the AR have been discovered, which result in increased basal activity of the receptor or widened ligand specificity.

For example, threonine to alanine mutation in amino acid 877 is the most frequently found mutation in PCa patients and converts flutamide, cyprotenone (steroidal anti-androgen), progesterone and oestrogens agonistic in AR. Mutation in amino acid 741 from tryptophan to either leucine or cysteine accounts for the switch of bicalutamide from anti-androgen to an agonist (Nara T, Miyazaki J, Araki H, Yamaoka M, Kanzaki N, Kusaka M, Miyamoto M. Novel mutations of androgen receptor: a possible mechanism of bicalutamide withdrawal syndrome. Cancer Res. 2003 Jan. 1; 63(1): 149-153.)

In addition to point mutations in AR, increased receptor levels can cause anti-androgens to function as agonists (Chen C D, Welsbie D S, Tran C, Baek S H, Chen R, Vessella R, Rosenfeld M G, Sawyers C L. Molecular determinants of resistance to antiandrogen therapy. Nat Med 2004 January; 10(1): 33-39). The antagonist-agonist conversion has significant clinical relevance. Approximately 30% of men with progressing PCa experience a paradoxical drop in serum prostate specific antigen levels after discontinuation of the anti-androgen treatment.

To date, treatment for CRPC has been disappointing with expected survival estimated at 7 to 16 months. Despite recent addition of two novel treatment options for CRPC, the therapeutic prostate cancer vaccine sipuleucel-T and novel testosterone synthesis inhibitor abiraterone acetate, efficient, novel agents that specifically target AR are still needed.

More specifically, there is a need for new anti-androgen compounds that are more potent than bicalutamide in antagonizing the activities of endogenous androgens on AR. There is also a need for new anti-androgen compounds that exhibit minimal agonism in AR. Importantly, there is a need for novel anti-androgens that do not gain agonistic activity in CRPC related mutant ARs or in CRPC related settings in which AR is present at high amounts. In addition, there is a need for non-steroidal, non-toxic molecules with drug-like properties that can be used in the treatment and prevention of BPH, PCa and CRPC.

Now it has been surprisingly found that the arylamide derivatives according to the present invention overcome the disadvantages related to bicalutamide and other arylamide derivatives known in the art.

SUMMARY OF THE INVENTION

The present invention provides new arylamide derivatives having formula (I)

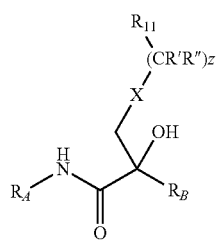

(I)

and N-oxides, stereoisomers and pharmaceutically acceptable salts thereof;

where
R' and R" are each independently selected from the group consisting of H and alkyl;
z is an integer 0 to 3;
X is selected from the group consisting of O, S, S(O), $SO_2$, NR12, where R12 is selected from the group consisting of H, alkyl, $COCH_3$ and COR, where R is hydrogen or alkyl; $CH_2$ and CO; or
when z is 0, then X may be N and forms together with R11 a heterocyclic ring selected from the group consisting of morpholine, 1,2,4-triazole, imidazole and N-substituted imidazole;
R11, when not forming a ring with X as defined above, is selected from the group consisting of alkyl, alkenyl, (per) haloalkyl, haloalkenyl, CN-alkyl and an aryl, heteroaryl, aliphatic or heteroaliphatic, 3-7-membered ring optionally substituted with 1-5 substituents selected from the group consisting of alkyl, alkoxy, hydroxy, halogen, (per)haloalkyl, CN, $NO_2$, COR, COOR, CONHR, $NR_2$, $NHCOCF_3$, NHCOR, NHCONHR, NHCOOR, OCONHR, $NHSO_2R$, $NHCSCH_3$, SR, SOR and $SO_2R$, where R is as defined above;
$R_B$ is a heteroaromatic ring having 6 ring members and being optionally substituted at one or more ring carbon atoms, of which ring members 1 or 2 are N atoms and the other ring members are carbon atoms, or
$R_B$ is an optionally substituted phenyl group,
the substituent(s) in $R_B$ being selected from the group consisting of alkyl, alkoxy, hydroxy, halogen, (per)haloalkyl, CN, $NO_2$, COR, COOR, CONHR, $NR_2$, $NHCOCF_3$, NHCOR, NHCONHR, NHCOOR, OCONHR, CONHR, where R is as defined above; $NHCSCH_3$, SR, SOR and $SO_2R$, where R is as defined above; or,
when $R_B$ is an optionally substituted phenyl group, then two adjacent substituents may also form with the carbon atoms, to which they are attached, a substituted or unsubstituted aliphatic, heteroaliphatic or heteroaromatic ring; and
$R_A$ is a mono- or bicyclic heteroaromatic ring system having 6 to 10 ring members and being optionally substituted at one or more ring carbon atoms, of which ring members 1 to 4 are N atoms and the other ring members are carbon atoms, whereby when $R_B$ is an optionally substituted phenyl group, then the ring attached to the NH group contains at least one N atom as a ring member, or
when $R_B$ is an optionally substituted heteroaromatic ring, then $R_A$ may also be an optionally substituted phenyl group,
the substituent(s) in $R_A$ being selected from the group consisting of alkyl, alkoxy, halogen, (per)haloalkyl, hydroxy, $(CH_2)_nCHO$, where n is an integer 0-6; CN, $NO_2$, COR, COOH and CONHR, where R is as defined above,
or when $R_A$ is an optionally substituted phenyl group, then two adjacent substituents may also form with the carbon atoms, to which they are attached, a substituted or unsubstituted aliphatic, heteroaliphatic or heteroaromatic ring.

The invention also relates to pharmaceutical compositions comprising an effective amount of one or more heteroarylamide derivatives of formula (I) or pharmaceutically acceptable salts thereof together with a suitable carrier and conventional excipients.

Further the invention relates to heteroarylamide derivatives of formula (I) or pharmaceutically acceptable salts thereof for use as a medicament.

The invention also relates to heteroarylamide derivatives of formula (I) or pharmaceutically acceptable salts thereof for use in the treatment of androgen receptor related diseases.

Finally the invention provides a process for preparing heteroarylamide derivatives of formula (I).

DETAILED DESCRIPTION OF THE INVENTION

The heteroarylamides of formula (I) according to the present invention possess at least one asymmetric carbon atom, i.e. the carbon atom, to which the hydroxyl is attached. Thus, the compounds exist in racemic form and optically active forms. All these forms are encompassed by the present invention.

By the term "alkyl", in the definition of the compound group of formula (I), is meant a linear or branched, saturated hydrocarbon chain containing 1 to 6 carbon atoms. The prefix "halo" means that such an alkyl group is halogenated with e.g. fluoro, chloro, bromo or iodo, partially or completely (per)halo.

By the term "alkoxy" is meant a linear or branched, saturated hydrocarbon chain containing 1 to 6 carbon atoms, one carbon atom being bound via a single bond to oxygen. Examples of alkoxy groups are methoxy, ethoxy, propoxy and butoxy.

By the term "alkenyl" is meant an unsaturated hydrocarbon chain having one or more double bonds and containing 2 to 6 carbon atoms.

By the term "aliphatic, heteroaliphatic or heteroaromatic ring" is meant a 4-7-membered ring, where 1-2 carbon atoms may be replaced by heteroatoms selected from O and S. Such a ring may be substituted with one or more substituents selected from the group consisting of alkyl, alkoxy, halogen, hydroxy, (per)haloalkyl, CN, NO$_2$, COR, COOR, CONHR, NR$_2$, NHCOCF$_3$, NHCOR, NHCONHR, NHCOOR, OCONHR, where R is hydrogen or alkyl; NHCSCH$_3$, SR, SOR and SO$_2$R, where R is hydrogen or alkyl; the substituent(s) being preferably CN, CF$_3$, F or Cl. Typical examples of groups formed by the rings falling under the term "aliphatic, heteroaliphatic or heteroaromatic ring" and the benzene ring, to which they are fused, are tetrahydronaphtalene and benzofuran.

By the term "an aryl, heteroaryl, aliphatic or heteroaliphatic, 3-7-membered ring" in the definition of R11 is meant saturated or unsaturated ring having 5 to 7 ring members, 0 to 3 of which being a heteroatom selected from O, S and N, the other members being carbon atoms. Typical examples of R11 as an above defined ring are phenyl, pyridyl, cyclopropyl, cyclobutyl, cyclopentyl, cyclohexyl, furyl and tetrahydrofuryl. The ring may be substituted with 1-5 substituents selected from the group consisting of alkyl, alkoxy, hydroxy, halogen, (per)haloalkyl, CN, NO$_2$, COR, COOR, CONHR, NR$_2$, NHCOCF$_3$, NHCOR, NHCONHR, NHCOOR, OCONHR, NHCSCH$_3$, SR, SOR and SO$_2$R, where R is hydrogen or alkyl; the substituent(s) being preferably CN, CF$_3$, F or Cl.

Examples of meanings for R$_B$ are those of the following formulae:

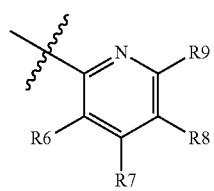

(a)

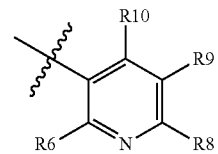

(b)

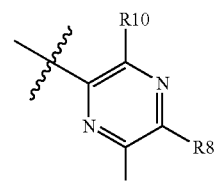

(c)

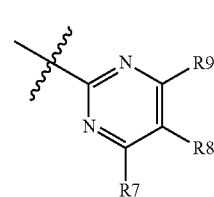

(d)

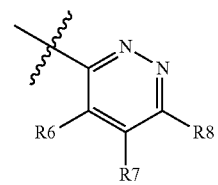

(e)

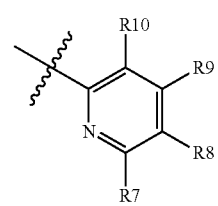

(f)

where R6-R10 are selected from the group consisting of hydrogen, alkyl, alkoxy, hydroxy, halogen, (per)haloalkyl, CN, NO$_2$, COR, COOR, NR$_2$, NHCOCF$_3$, NHCOR, NHCONHR, NHCOOR, OCONHR, CONHR, where R is hydrogen or alkyl; NHCSCH$_3$, SR, SOR and SO$_2$R, where R is hydrogen or alkyl.

R$_B$ may also be an optionally substituted phenyl group of formula

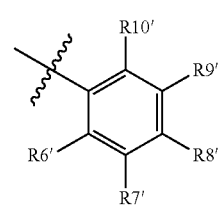

(g)

where R6'-R10' are selected from the group consisting of hydrogen, alkyl, alkoxy, hydroxy, halogen, (per)haloalkyl, CN, NO$_2$, COR, COOR, NR$_2$, NHCOCF$_3$, NHCOR, NHCONHR, NHCOOR, OCONHR, CONHR, where R is hydrogen or alkyl; NHCSCH$_3$, SR, SOR and SO$_2$R, where R is hydrogen or alkyl, or two adjacent substituents may also form with the carbon atoms, to which they are attached, a substituted or unsubstituted aliphatic, heteroaliphatic or heteroaromatic ring.
Examples of $R_A$ being a mono- or bicyclic heteroaromatic ring system having 6 to 10 ring members are those of the following formulae:
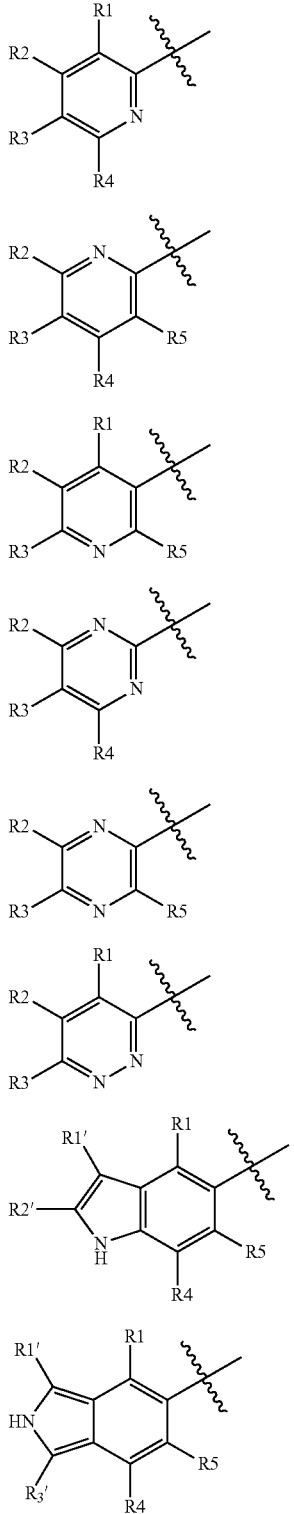
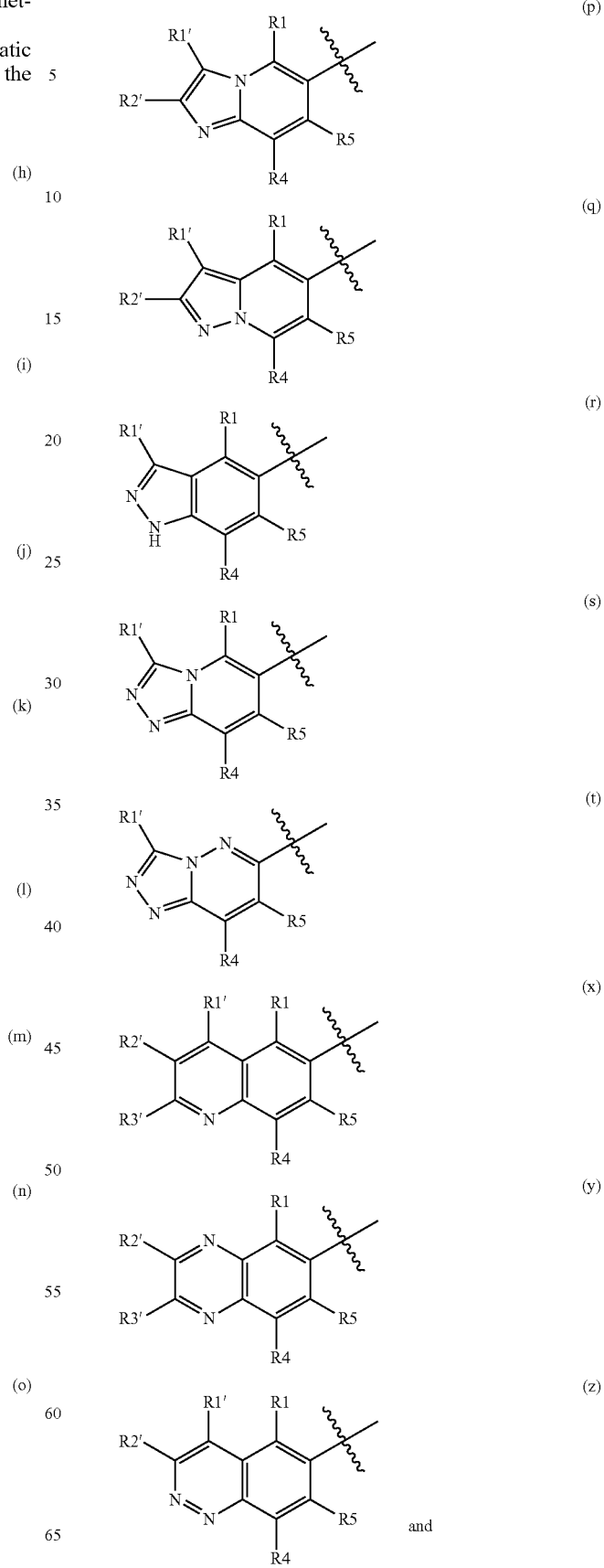

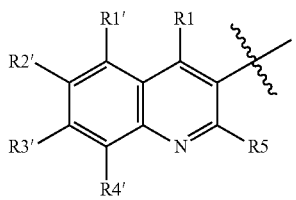

(aa)

where R1 to R5 and R1' to R4' are selected from hydrogen, alkyl, alkoxy, hydroxy, halogen, (per)haloalkyl, $(CH_2)_n$CHO, where n is an integer 0-6; CN, $NO_2$, COR, COOR and CONHR, where R is hydrogen or alkyl.

When $R_B$ is a heteroaromatic ring having 6 ring members, then $R_A$ may also be an optionally substituted phenyl group of formula

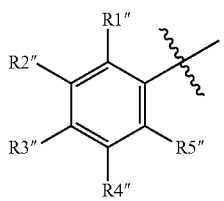

(gg)

where R1"-R5" are selected from the group consisting of hydrogen, alkyl, alkoxy, halogen, (per)haloalkyl, hydroxy, $(CH_2)_n$CHO, where n is an integer 0-6; CN, $NO_2$, COR, COOR and CONHR, where R is hydrogen or alkyl, or two adjacent substituents may also form with the carbon atoms, to which they are attached, a substituted or unsubstituted aliphatic, heteroaliphatic or heteroaromatic ring.

Preferred compounds of formula (I) are those where z is 0 or 1.

Preferred are also those wherein R11 is alkyl, especially methyl, ethyl, isopropyl, isopentyl, or tert-butyl, more preferably methyl, ethyl or isopropyl, most preferably methyl or ethyl, or phenyl optionally substituted with halo, especially chloro. Further preferred are compounds of formula (I) wherein R11 is cyclopropyl.

Further preferred heteroarylamides of the present invention are those of formula (I) where $R_A$ is an optionally substituted phenyl and $R_B$ is an optionally substituted pyridyl.

Another preferred group of compounds of formula (I) comprises those where $R_A$ is optionally substituted pyridyl or optionally substituted triazolo[4,3-b]pyridazinyl and $R_B$ is optionally substituted phenyl.

Preferred substituents in $R_A$ and $R_B$ are cyano, halo, especially chloro and fluoro, and haloalkyl, especially trifluoromethyl.

Preferred compounds are those of formulae (I-a), (I-b) and (I-c)

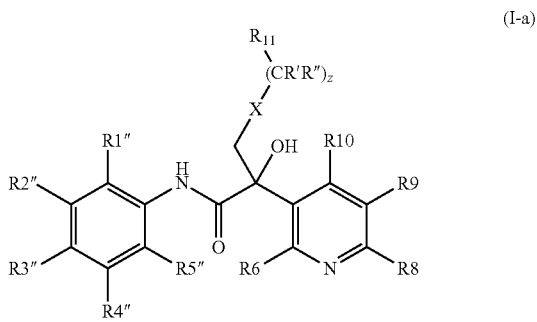

(I-a)

wherein R1"-R5", R6, R8, R9, R10, R11, R', R", X and z are as defined above,

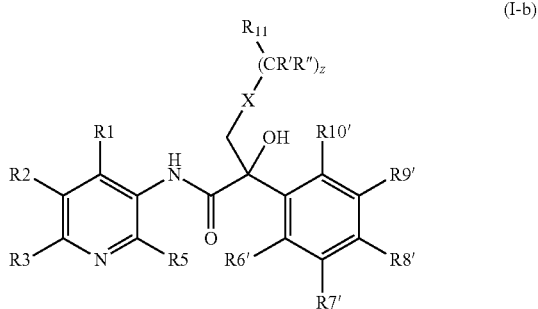

(I-b)

wherein R1, R2, R3, R5, R6'-R10', R11, R', R", X and z are as defined above;

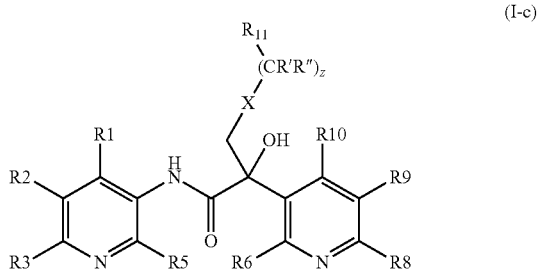

(I-c)

wherein R1, R2, R3, R5, R6, R8, R9, R10, R11, R', R", X and z are as defined above;
and pharmaceutically acceptable salts thereof.

Preferred compounds of formula (I-a) are those wherein R1", R4", R5", R6 and R10 are hydrogen; R2" is trifluoromethyl or halo, especially chloro; R3" is cyano; R8 is $CF_3$ or halo, preferably halo, especially chloro or fluoro; R9 is hydrogen or halo, especially fluoro; z is 0 or 1 (R'=R"=H); X is $SO_2$; and R11 is alkyl, especially methyl, ethyl, tert-butyl, cyclopropyl, isopropyl, or isopentyl, preferably ethyl or methyl, more preferably ethyl, or phenyl or pyridinyl, preferably phenyl, optionally substituted with halo, especially chloro, when z is 0, or phenyl optionally substituted with halo, especially chloro, when z is 1.

Preferred compounds of formula (I-b) are those wherein R1, R5, R6' and R10' are hydrogen; R2 is trifluoromethyl or halo, especially chloro; R3 is cyano; R8' is halo, especially chloro or fluoro; R9' is hydrogen or halo, especially fluoro; z is 0; X is $SO_2$; and R11 is alkyl, especially methyl, ethyl, tert-butyl, cyclopropyl, isopropyl, or isopentyl, preferably methyl or ethyl, preferably ethyl.

Preferred compounds of formula (I-c) are those wherein R1, R5, R6, R7 and R10 are hydrogen; R2 is trifluoromethyl or halo, especially chloro; R3 is cyano; R8 is halo, especially chloro or fluoro; R9 is hydrogen or halo, especially fluoro; z is 0; X is $SO_2$; and R11 is alkyl, especially isopropyl.

Examples of particularly preferred specific compounds are:

2-(6-chloropyridin-3-yl)-N-[4-cyano-3-(trifluoromethyl) phenyl]-3-(ethanesulfonyl)-2-hydroxypropanamide;
2-cyano-5-[3-(ethylsulfonyl)-2-(4-fluorophenyl)-2-hydroxypropanamido]-3-(trifluoromethyl)pyridine-1-oxide;
N-[6-cyano-5-(trifluoromethyl)pyridin-3-yl]-3-(ethanesulfonyl)-2-(4-fluorophenyl)-2-hydroxypropanamide;
5-[2-(4-chlorophenyl)-3-(ethylsulfonyl)-2-hydroxypropanamido]-2-cyano-3-(trifluoromethyl)pyridine-1-oxide;

2-(4-chlorophenyl)-N-[6-cyano-5-(trifluoromethyl)pyridin-3-yl]-3-(ethanesulfonyl)-2-hydroxypropanamide;
2-(6-chloropyridin-3-yl)-N-[4-cyano-3-(trifluoromethyl)phenyl]-2-hydroxy-3-[(3-methylbutane)sulfonyl]propanamide;
2-(3,4-difluorophenyl)-3-(ethanesulfonyl)-2-hydroxy-N-[3-(trifluoromethyl)-[1,2,4]triazolo[4,3-b]pyridazin-6-yl]propanamide;
N-(3-chloro-4-cyanophenyl)-3-{[(4-chlorophenyl)methane]sulfonyl}-2-(6-chloropyridin-3-yl)-2-hydroxypropanamide;
N-(3-chloro-4-cyanophenyl)-3-[(4-chlorobenzene)sulfonyl]-2-(6-chloropyridin-3-yl)-2-hydroxypropanamide;
3-(ethanesulfonyl)-2-(4-fluorophenyl)-2-hydroxy-N-[3-(trifluoromethyl)-[1,2,4]triazolo[4,3-b]pyridazin-6-yl]propanamide;
2-(4-chlorophenyl)-3-(ethanesulfonyl)-2-hydroxy-N-[3-(trifluoromethyl)-[1,2,4]triazolo[4,3-b]pyridazin-6-yl]propanamide;
2-(6-chloropyridin-3-yl)-N-[4-cyano-3-(trifluoromethyl)phenyl]-2-hydroxy-3-(propane-2-sulfonyl)propanamide;
2-(6-chloropyridin-3-yl)-N-[6-cyano-5-(trifluoromethyl)pyridin-3-yl]-2-hydroxy-3-(propane-2-sulfonyl)propanamide;
2-chloro-5-{1-[(3-chloro-4-cyanophenyl)amino]-3-[(4-chlorophenyl)sulfonyl]-2-hydroxy-1-oxopropan-2-yl}pyridine 1-oxide;
N-(3-chloro-4-cyanophenyl)-3-(4-fluorobenzenesulfonyl)-2-hydroxy-2-[6-(trifluoromethyl)pyridin-3-yl]propanamide;
N-(3-chloro-4-cyanophenyl)-2-(6-chloropyridin-3-yl)-3-[(6-chloropyridin-3-yl)sulfonyl]-2-hydroxypropanamide;
2-(6-chloropyridin-3-yl)-N-[4-cyano-3-(trifluoromethyl)phenyl]-2-hydroxy-3-(2-methylpropane-2-sulfonyl)propanamide;
2-(6-chloropyridin-3-yl)-N-[4-cyano-3-(trifluoromethyl)phenyl]-3-(cyclopropanesulfonyl)-2-hydroxypropanamide;
2-(6-chloropyridin-3-yl)-N-[4-cyano-3-(trifluoromethyl)phenyl]-2-hydroxy-3-methanesulfonylpropanamide;
5-{3-(tert-butylsulfonyl)-1-[(4-cyano-3-(trifluoromethyl)phenyl)amino]-2-hydroxy-1-oxopropan-2-yl}-2-chloropyridine 1-oxide;
and pharmaceutically acceptable salts thereof.

Pharmaceutically acceptable salts and their preparation are well-known in the art.

The arylamides of the invention may be prepared by methods described below. For example the compounds of formula (I), where X is O, SO or SO$_2$, may be prepared by reacting an epoxy compound of formula (5),

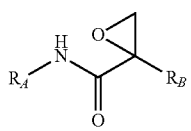

where R$_A$ and R$_B$ are as defined above, with a compound of formula (II),

R11-(CR'R'')$_z$—X'H     (II)

where R11, R', R'' and z are as defined above and X' is O or S, to obtain a compound of formula (I), where X is O or S, and, if desired, oxidizing the obtained compound where X is S to obtain a compound of formula (I), where X is SO or SO$_2$. The process is preferably carried out via the following reaction steps:

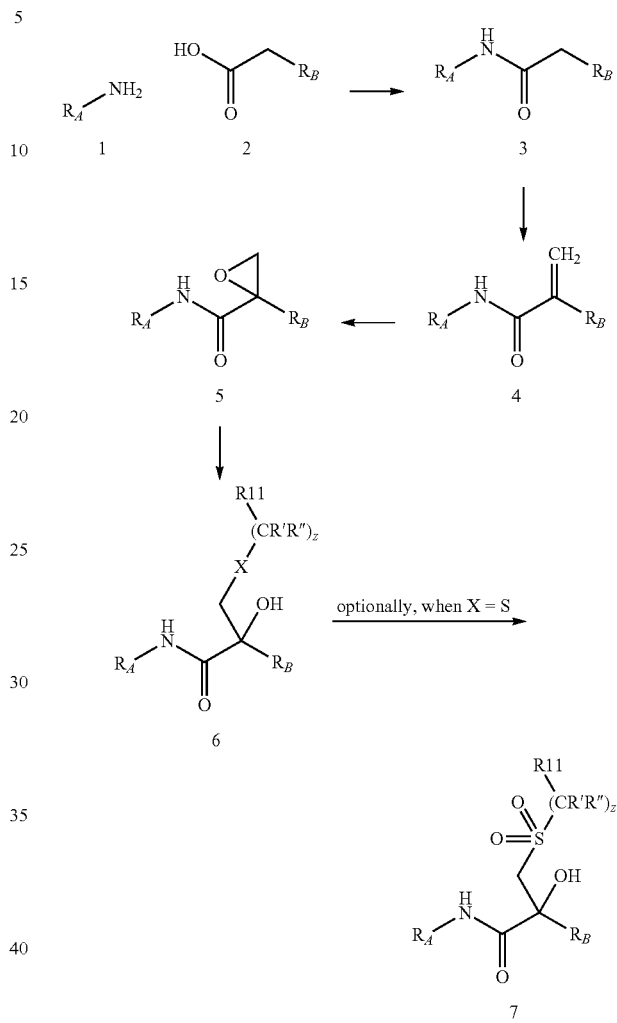

General Synthesis Procedure

The compounds of the present invention were synthesized using commercially available amines, (het)arylacetic acids and phenols, and thiols, as starting materials. 5-amino-3-(trifluoromethyl)pyridine-2-carbonitrile was prepared according to the method described in WO 2008/119015. 3-(trifluoromethyl)-[1,2,4]triazolo[4,3-b]pyridazin-6-amine was prepared according to the method described in WO 2011/103202.

General Method for the Synthesis of the Intermediate (3)

Method-3A: A corresponding phenyl acetic acid (2) (0.58 mmol) and aniline (1) (0.58 mmol) was dissolved in DMF (1 ml). 1.16 mmol of HATU (2 equivalents) was added and the mixture was stirred for 5 minutes. 1.75 mmol of TEA (3 equivalents) was added at RT and the resulting mixture stirred for 16 hours. After completion of the reaction confirmed by TLC water was added (5 ml). The mixture was extracted with EtOAc. Organic layer was washed with diluted HCl (3×15 ml), dried over sodium sulphate and concentrated to get crude intermediate (3). Intermediate (3) was purified by flash chromatography.

Method-3B: A corresponding phenyl acetic acid (2) (0.14 mmol) was dissolved in dichloromethane (5 ml) and cooled in an ice bath to −5-0° C. 0.42 mmol (3 equivalents) of thionylchloride was dropped in dichloromethane while keeping the temperature at +5-0° C. After addition was complete the ice bath was removed and the mixture was allowed to warm to room temperature (RT). After stirring for 4 hours, the mixture was cooled to 0° C. and the aniline (1) (0.13 mmol, 0.9 equivalents) was added in dimethylacetamide (2 ml). The resulting mixture was stirred at RT and monitored by TLC. After completion of the reaction, the mixture was poured in ice water and extracted with dichloromethane. The Organic phase was washed with water and dried over $Na_2SO_4$ and evaporated to give (3) after flash chromatography.

Method-3C: Aniline (0.053 mmol) and acetic acid (0.080 mmol, 1.5 equivalents) was dissolved in THF (0.15 ml). T3P (propylphosphonic anhydride) was added (0.13 mmol, 2.5 equivalents). The resulting mixture was stirred and 0.106 mmol of DIPEA (2 equivalents) was added. After addition the mixture was stirred at RT for 5 h. After completion of the reaction the mixture was diluted with AcOEt and the organic layer was washed with water. Organic layer was separated, dried over sodium sulphate and concentrated under reduced pressure to give (3).

General Method for the Synthesis of the Intermediate (4)

0.15 mmol of (3), 0.30 mmol (2 equivalents) of paraformaldehyde and 0.041 g of $K_2CO_3$ was mixed in NMP (N-methyl pyrrolidone, 1 ml). The mixture was heated to 90° C. and stirred for 30 minutes. After cooling to RT 10 ml of water was added and the mixture was extracted with diethyl ether (2×10 ml). The organic phase was washed with water (1×10 ml) and evaporated to give (4). The product was purified by flash chromatography.

General Method for the Synthesis of the Intermediate (5)

0.057 mmol of (4), 0.10 mmol of $CH_3CN$ (1.8 equivalents), and $KHCO_3$ (0.01 mmol, 0.175 equivalents) was mixed in MeOH (ml). $H_2O_2$ (0.057 mmol) was added dropwise. After addition the resulting mixture was stirred at RT for 2 h. Water was added and the resulting mixture was extracted with EtOAc. The organic phase was concentrated to give the epoxide (5). Product was used without further purification for the synthesis of (6).

General Method for the Synthesis of (6)

To 0.9 (3 equivalents) mmol of $K_2CO_3$ in dry THF (7.5 ml), 0.45 mmol (1.5 equivalents) of a corresponding thiophenol or thiol was added at 0° C. Mixture was stirred at 0° C. for 30 min. 0.3 mmol of the epoxide (5) in dry THF (7.5 ml) was added at 0° C. The resulting mixture was stirred at RT for 14 h. After completion of the reaction confirmed by TLC water was added. The resulting mixture was extracted with EtOAc. The organic phase was concentrated to get the crude material which was used for the synthesis of (7) without further purification. In case of volatile thiols, an excess up to 10 equivalents was used.

General Method for the Synthesis of (7)

0.047 mmol of (6) was dissolved in $CH_2Cl_2$ (8 ml). 70% MCPBA (0.14 mmol, 3 equivalents) was added and the mixture was stirred at RT. After completion of the reaction monitored by TLC reaction was quenched by saturated sodium sulphite solution in water and extracted with dichloromethane. The organic layer was washed with saturated sodium sulphite solution, dried over $Na_2SO_4$ and evaporated. Products were purified using flash chromatography.

Preparation of Sulfinyl Compounds

The sulfinyl compounds of the present invention can be made from the corresponding intermediate (6) according to the procedure described by Bhise et al. in Synthetic communications, 2009, 39, 1516-1526 using sodium perborate trihydrate as an oxidation agent.

Preparation of Aromatic Amines from Epoxide (5)

The aromatic amines of the present invention can be made from the corresponding intermediate (5) according to the procedure described by Dalton et al. in US 2006/0241180.

Preparation of Aliphatic Amines from Epoxide (5)

The aliphatic amines of the present invention can be made from the corresponding intermediate (5) using similar method as described in case of thiols and phenols, but NaH was used as base in the reactions.

Preparation of Cyclopropylthiol

Cyclopropylthiol was prepared according to the method described in JAGS 1992, 114(9), 3492-3499

EXAMPLES

The compounds listed in Table 1 below were prepared using the synthesis procedure described above and illustrate the present invention.

TABLE 1

| Ex | Name | LCMS, NMR |
| --- | --- | --- |
| 1 | 2-(6-chloropyridin-3-yl)-N-[4-cyano-3-(trifluoromethyl)phenyl]-3-(ethanesulfonyl)-2-hydroxypropanamide | 1H NMR (CDCl3): 1.43 (3H, t, J = 7.4 Hz), 3.00-3.15 (2H, m), 3.48 (1H, d, J = 14.8 Hz), 4.17 (1H, d, J = 14.8 Hz), 6.01 (1H, s), 7.38 (1H, m), 7.80 (1H, m), 7.88 (1H, m), 7.97 (1H, m), 8.06 (1H, m), 8.74 (1H, m), 9.01 (1H, bs). |
| 2 | 2-cyano-5-[3-(ethylsulfonyl)-2-(4-fluorophenyl)-2-hydroxypropanamido]-3-(trifluoromethyl)pyridine-1-oxide | 1H NMR (CDCl3): 1.33 (3H, t, J = 7.5 Hz), 3.01 (2H, m), 3.49 (1H, d, J = 14.8 Hz), 4.21 (1H, d, J = 14.8 Hz), 5.93 (1H, s), 7.02 (2H, m), 7.61 (2H, m), 7.88 (1H, m), 8.51 (1H, m), 8.94 (1H, m), 9.65 (1H, bs). |
| 3 | N-[6-cyano-5-(trifluoromethyl)-pyridin-3-yl]-3-(ethanesulfonyl)-2-(4-fluorophenyl)-2-hydroxypropanamide | LC-MS: m/z 444 |
| 4 | 5-[2-(4-chlorophenyl)-3-(ethylsulfonyl)-2-hydroxypropanamido]-2-cyano-3-(trifluoromethyl)pyridine-1-oxide | 1H NMR (CDCl3): 1.31 (3H, t, J = 7.5 Hz), 3.02 (2H, m), 3.47 (1H, d, J = 14.8 Hz), 4.20 (1H, d, J = 14.8 Hz), 6.03 (1H, s), 7.29 (2H, m), 7.54 (2H, m), 8.49 (1H, m), 8.89 (1H, m), 9.70 (1H, bs). |
| 5 | 2-(4-chlorophenyl)-N-[6-cyano-5-(trifluoromethyl)pyridin-3-yl]-3-(ethanesulfonyl)-2-hydroxypropanamide | LC-MS: m/z 460 |

TABLE 1-continued

| Ex | Name | LCMS, NMR |
|---|---|---|
| 6 | 2-(6-chloropyridin-3-yl)-N-[4-cyano-3-(trifluoromethyl)phenyl]-2-hydroxy-3-[(3-methylbutane)sulfonyl-]propanamide | 1H NMR (CDCl3): 0.92 (6H, m), 1.60-1.78 (3H, m), 3.00 (2H, m), 3.49 (1H, d, J = 14.8 Hz), 4.16 (1H, d, J = 14.8 Hz), 6.04 (1H, s), 7.37 (1H, m), 7.80 (1H, m), 7.86 (1H, m), 7.98 (1H, m), 8.08 (1H, m), 8.74 (1H, m), 9.03 (1H, bs). |
| 7 | 2-(3,4-difluorophenyl)-3-(ethanesulfonyl)-2-hydroxy-N-[3-(trifluoromethyl)-[1,2,4]triazolo[4,3-b]pyridazin-6-yl]propanamide | 1H NMR (CDCl3): 1.42 (3H, t, J = 7.4 Hz), 2.93-3.13 (2H, m), 3.53 (1H, d, J = 14.9 Hz), 4.14 (1H, d, J = 14.9 Hz), 5.96 (1H, s), 7.22 (1H, m), 7.45 (1H, m), 7.58 (1H, m), 8.23 (1H, m), 8.43 (1H, m), 9.41 (1H, bs). |
| 8 | N-(3-chloro-4-cyanophenyl)-3-{[(4-chlorophenyl)methane]sulfonyl}-2-(6-chloropyridin-3-yl)-2-hydroxy-propanamide | 1H NMR (CDCl3): 3.21 (1H, d, J = 15.1 Hz), 4.13 (1H, d, J = 15.1 Hz), 4.24 (1H, d, J = 14.0 Hz), 4.46 (1H, d, J = 14.0 Hz), 5.74 (1H, s), 7.36 (1H, m), 7.41 (2H, m), 7.47 (3H, m), 7.64 (1H, m), 7.88 (1H, m), 7.95 (1H, m), 8.66 (1H, m), 8.83 (1H, bs). |
| 9 | N-(3-chloro-4-cyanophenyl)-3-[(4-chlorobenzene)sulfonyl]-2-(6-chloropyridin-3-yl)-2-hydroxy-propanamide | 1H NMR (CDCl3) 3.86 (1H, d, J = 14.8 Hz), 4.16 (1H, d, J = 14.8 Hz), 6.00 (1H, s), 7.19 (1H, m), 7.37 (1H, m), 7.43 (2H, m), 7.60 (1H, m), 7.64 (2H, m), 7.77 (2H, m), 8.61 (1H, m), 8.90 (1H, bs). |
| 10 | 3-(ethanesulfonyl)-2-(4-fluoro-phenyl)-2-hydroxy-N-[3-(trifluoro-methyl)-[1,2,4]triazolo[4,3-b]-pyridazin-6-yl]propanamide | 1H NMR (CDCl3): 1.40 (3H, t, J = 7.4 Hz), 2.80-3.10 (2H, m), 3.59 (1H, d, J = 15.0 Hz), 4.13 (1H, d, J = 15.0 Hz), 5.88 (1H, s), 7.13 (2H, m), 7.69 (2H, m), 7.21 (1H, m), 8.44 (1H, m), 9.41 (1H, bs). |
| 11 | 2-(4-chlorophenyl)-3-(ethanesulfonyl)-2-hydroxy-N-[3-(trifluoro-methyl)-[1,2,4]triazolo[4,3-b]-pyridazin-6-yl]propanamide | 1H NMR (CDCl3): 1.40 (3H, t, J = 7.4 Hz), 2.85-3.10 (2H, m), 3.58 (1H, d, J = 15.0 Hz), 4.13 (1H, d, J = 15.0 Hz), 5.88 (1H, s), 7.41 (2H, m), 7.64 (2H, m), 7.21 (1H, m), 8.43 (1H, m), 9.40 (1H, bs). |
| 12 | 2-(6-chloropyridin-3-yl)-N-[4-cyano-3-(trifluoromethyl)phenyl]-2-hydroxy-3-(propane-2-sulfonyl)propan-amide | 1H NMR (CDCl3): 1.39 (3H, d, J = 6.9 Hz), 1.43 (3H, d, J = 6.8 Hz), 3.15 (1H, m) 3.48 (1H, d, J = 14.5 Hz), 4.14 (1H, d, J = 14.5 Hz), 6.05 (1H, s), 7.37 (1H, m), 7.79 (1H, m), 7.88 (1H, m), 7.97 (1H, m), 8.04 (1H, m), 8.74 (1H, m), 9.03 (1H, bs). |
| 13 | 2-(6-chloropyridin-3-yl)-N-[6-cyano-5-(trifluoromethyl)pyridin-3-yl]-2-hydroxy-3-(propane-2-sulfonyl)-propanamide | 1H NMR (CDCl3): 1.38 (3H, d, J = 6.9 Hz), 1.43 (3H, d, J = 6.8 Hz), 3.15 (1H, m) 3.47 (1H, d, J = 14.6 Hz), 4.16 (1H, d, J = 14.6 Hz), 7.37 (1H, m), 7.97 (1H, m), 8.72 (1H, m), 8.74 (1H, m), 8.88 (1H, m), 9.33 (1H, bs). |
| 14 | 2-chloro-5-{1-[(3-chloro-4-cyanophenyl)amino]-3-[(4-chlorophenyl)sulfonyl]-2-hydroxy-1-oxopropan-2-yl}pyridine 1-oxide | 1H NMR (CDCl3) 3.78 (1H, d, J = 14.7 Hz), 4.16 (1H, d, J = 14.7 Hz), 6.24 (1H, s), 7.37 (3H, m), 7.47 (2H, m), 7.61 (1H, m), 7.73 (2H, m), 7.79 (1H, m), 8.67 (1H, m), 9.01 (1H, bs). |
| 15 | N-(3-chloro-4-cyanophenyl)-3-(4-fluorobenzenesulfonyl)-2-hydroxy-2-[6-(trifluoromethyl)pyridin-3-yl]propanamide | 1H NMR (CDCl3) 3.95 (1H, d, J = 14.8 Hz), 4.17 (1H, d, J = 14.8 Hz), 6.14 (1H, s), 7.12 (2H, m), 7.41 (1H, m), 7.45-7.75 (5H, m), 7.80 (1H, m), 8.05 (1H, m), 8.94 (1H, bs). |
| 16 | N-(3-chloro-4-cyanophenyl)-2-(6-chloropyridin-3-yl)-3-[(6-chloropyridin-3-yl)sulfonyl]-2-hydroxypropanamide | 1H NMR (CDCl3) 3.86 (1H, d, J = 14.9 Hz), 4.26 (1H, d, J = 14.9 Hz), 5.81 (1H, s), 7.27 (1H, m), 7.38 (1H, m), 7.45 (1H, m), 7.61 (1H, m), 7.75 (1H, m), 7.81 (1H, m), 7.94 (1H, m), 8.61 (1H, m), 8.71 (1H, m), 8.85 (1H, bs). |
| 17 | 2-(6-chloropyridin-3-yl)-N-[4-cyano-3-(trifluoromethyl)phenyl]-2-hydroxy-3-(2-methylpropane-2-sulfonyl)propanamide | 1H NMR (CDCl3): 1.44 (9H, s), 3.54 (1H, d, J = 13.6 Hz), 4.05 (1H, d, J = 13.6 Hz), 6.03 (1H, s), 7.36 (1H, m), 7.78 (1H, m), 7.89 (1H, m), 8.01 (1H, m), 8.05 (1H, m) 8.77 (1H, m), 9.08 (1H, bs). |
| 18 | 2-(6-chloropyridin-3-yl)-N-[4-cyano-3-(trifluoromethyl)phenyl]-3-(cyclopropanesulfonyl)-2-hydroxypropanamide | 1H NMR (CDCl3): 1.00 (2H, m), 1.20 (2H, m), 2.49 (1H, m), 3.62 (1H, d, J = 14.6 Hz), 4.31 (1H, d, J = 14.6 Hz), 6.73 (1H, s), 7.30 (1H, m), 7.72 (1H, m), 7.95 (2H, m), 8.08 (1H, m), 8.70 (1H, m), 9.63 (1H, bs). |
| 19 | 2-(6-chloropyridin-3-yl)-N-[4-cyano-3-(trifluoromethyl)phenyl]-2-hydroxy-3-methanesulfonylpropanamide | 1H NMR (CDCl3): 3.03 (3H, s), 3.56 (1H, d, J = 15.2 Hz), 4.24 (1H, d, J = 15.2 Hz), 5.93 (1H, s), 7.39 (1H, m), 7.80 (1H, m), 7.87 (1H, m), 7.96 (1H, m), 8.06 (1H, m) 8.73 (1H, m), 9.00 (1H, bs). |

TABLE 1-continued

| Ex | Name | LCMS, NMR |
| --- | --- | --- |
| 20 | 5-{3-(tert-butylsulfonyl)-1-[(4-cyano-3-(trifluoromethyl)phenyl)amino]-2-hydroxy-1-oxopropan-2-yl}-2-chloropyridine 1-oxide | 1H NMR (CDCl3): 1.40 (9H, s), 3.60 (1H, d, J = 13.6 Hz), 4.05 (1H, d, J = 13.6 Hz), 6.46 (1H, s), 7.51 (1H, m), 7.59 (1H, m), 7.76 (1H, m), 7.99 (1H, m), 8.16 (1H, m) 8.86 (1H, m), 9.63 (1H, bs). |

General Description of the Pharmacological Properties of the Compounds of the Present Invention The arylamide derivatives of the present invention show high antagonistic activity in AR. Antagonistic activity in AR refers to potency of the compound to compete and/or inhibit the activity of natural AR ligands such as dihydrotestosterone (DHT) and testosterone. The present invention provides compounds having antagonistic activity in AR to compete and/or inhibit the activity of non-natural AR ligands, such as synthetic androgens or anti-androgens used as medicaments (but which may exert deleterious side-effects).

Further, the present invention provides compounds that demonstrate potent anti-androgen activity in a dose-dependent manner. A major disadvantage of bicalutamide is incomplete AR antagonism. In the case of bicalutamide, increasing concentrations do not provide significant extra benefit (see Table 2). More potent anti-androgens than bicalutamide may be needed to treat advanced stage of PCa characterized by elevation of AR levels, thus there is a need for potent anti-androgens that can compensate for the elevated AR levels in a dose-dependent manner. The present invention provides compounds that exert minimal agonistic effects in AR.

The compounds of the present invention can be used to treat AR-related diseases, such as BPH and PCa. The compounds can also be used to treat CRPC. Further, the compounds can be used in combination with other anti-androgen treatments.

The compounds of the present invention do not gain agonistic activity in CRPC related mutations. By CRPC related mutations, all mutations that affect the development, progression or severity of the disease are referred. The CRPC related mutation may have resulted from androgen deprivation-induced enrichment of prostate cancer cells harboring the said mutation. For instance tryptophan 741 to leucine or to cysteine mutation and also threonine 877 to alanine mutation are referred.

The compounds of the present invention retain their antagonistic activities when AR levels are elevated.

The following tests and results are provided as to demonstrate the present invention in an illustrative way and should not be considered as limiting in the scope of invention. Further, the concentrations of the compounds in the assays are exemplary and should not be taken as limiting. A person skilled in the art may define pharmaceutically relevant concentrations with methods known in the art.

Experiments

To elucidate the potency of the compounds of the present invention to function as anti-androgens and to demonstrate that the compounds of the present invention retain their antagonistic activity in conditions known to confer agonistic activities in the first-line anti-androgen medications in clinical use (such as flutamide or bicalutamide, BIC) a series of in vitro studies was designed. These studies were based on measuring AR transactivation using a reporter gene assay, which is a well-established, golden standard assay in AR research. Depending on the presence or absence of natural AR ligand such as testosterone, this reporter gene assay can be used to determine both antagonistic and agonistic activity of the compounds. BIC was used as a reference compound in all studies representing currently available standard anti-androgen treatment.

AR Transactivation Assay

COS-1 cells (American Type Culture Collection, ATCC) were cultured in Dulbecco's Modified Eagle Medium (DMEM) supplemented with 10% fetal bovine serum (FBS), penicillin (6.25 U/ml) and streptomycin (6.25 µg/ml) and seeded onto 48-well plates (50 000 cells/well) one day before transfection. Transfection media containing 2.5% charcoal-stripped FBS in DMEM was changed on cells 4 h prior to transfection. Cells were transfected with 50 ng of luciferase (LUC) reporter gene plasmid (pPB-286/+32-LUC; PB, probasin promoter), 5 ng of AR expression plasmid (pSG5-hAR), and 5 ng of pCMVβ (an internal, beta-galactosidase control for transfection efficiency and cell growth) using TransIT-LT1 reagent (Mirus Bio Corporation) according to the manufacturer's instructions. One day after transfection, triplicate wells received either (i) vehicle (EtOH-DMSO), (ii) 50 nM testosterone (reference agonist, from Makor or Steraloids Inc.), (iii) increasing concentrations of BIC (reference antagonist) or (iv) compound of the present invention alone (to test for agonism) or (v) increasing concentrations of BIC (reference antagonist) or (vi) compound of the present invention together with the reference agonist in a competitive setting (50 nM; to test for antagonism of testosterone induced AR transcription). After 18 h, reporter gene activities (LUC and beta-galactosidase) were determined according to standard methods. The data are expressed as relative LUC activity (luciferase light units divided by beta-galactosidase $A420_{nm}$ to control for transfection efficiency) of a given compound in relation to the activity of a reference test item (=100%).

Alternatively, commercial Human AR Reporter Assay System (INDIGO Biosciences) was used. In this assay, non-human mammalian cells are engineered to express human WT AR together with LUC reporter gene linked to AR-responsive promoter. 400 pM 6-alpha-Fl testosterone, FIT, was used as a reference agonist in a competitive setting. The two reporter gene systems resulted in comparable data.

Agonism in WT AR

Agonism in WT AR of compounds of the present invention was measured in AR transactivation assay in COS-1 cells by exposing the transfected cells to test compounds alone as described above. Testosterone was used as a reference agonist. Relative LUC activity representing the level of AR activation was measured. The response obtained by the reference agonist was set as 100%. The compounds of the present invention did not show agonism in WT AR.

Antagonism in Wild Type (WT) AR

Antagonism in WT AR of compounds of the present invention was measured in AR transactivation assay in COS-1 cells in competitive setting using testosterone as a reference agonist as described above. Alternatively INDIGO Bioscience's Human AR Reporter Assay System was utilized. Known anti-androgen BIC was used as a reference antagonist. Relative LUC activity representing AR-dependent transcription obtained by exposure to reference agonist alone was set to 100%. The compounds of the present invention were efficient antagonists in WT AR (Table 2).

TABLE 2

Antagonism in WT AR

| Ex | Relative LUC activity (%) indicating residual androgen activity in relation to reference agonist (100%) | |
|---|---|---|
|  | 1 microM | 10 microM |
| 1 | 37 | 8 |
| 6 | 28 | 7 |
| 8 | 32 | 4 |
| 9 | 25 | 13 |
| 12 | 30 | 5 |
| 15 | 25 | 3 |
| BIC | 25 | 13 |

One of the major limitations in the use of currently available anti-androgens, such as flutamide and BIC, is the antagonist-agonist conversion observed in mutated AR.

Agonism in W741L Mutant AR

Agonism in W741L AR of compounds of the present invention was measured in AR transactivation assay in COS-1 cells as described above except that AR expression vector harboring the W741L mutation was used instead of the WT AR. The transfected cells were exposed to test compounds alone. BIC was used as a reference compound. As reported in literature, BIC functions as an agonist in this mutant AR variant and the relative LUC activity representing AR-dependent transcription induced by BIC was set to 100%. The compounds of the present invention did not show agonism in W741L AR (Table 3).

Agonism in T877A Mutant AR

Agonism in T877A AR of compounds of the present invention was measured in AR transactivation assay in COS-1 cells as described above except that AR expression vector harboring the T877A mutation was used. The transfected cells were exposed to test compounds alone. Testosterone was used as reference agonist, and its' relative LUC activity representing AR-dependent transcription was set to 100%. The compounds of the present invention did not show agonism in T877A AR (Table 3).

TABLE 3

Agonism in W741L and T877A mutant AR

| Ex | Relative LUC activity (%) in W741L AR in relation to BIC (100%) 10 microM | Relative LUC activity (%) in T877A AR in relation to testosterone (100%) 10 microM |
|---|---|---|
| 1 | 6 | 13 |
| 6 | 31 | 4 |
| 8 | 4 | 2 |
| 9 | 23 | 3 |
| 12 | 3 | 4 |
| BIC | 100 | 14 |

Gene Expression in VCaP Cells

Quantitative RT-PCR was used to study the ability of the compounds of the present invention to inhibit AR target gene expression. VCaP cells were seeded onto 12-well plates ($3\times10^5$ cells/well) and triplicate wells were treated with either (i) vehicle (EtOH-DMSO), or (ii) 1 nM R1881 (reference agonist, Perkin-Elmer), or (iii) increasing concentrations of BIC (reference antagonist), or (iv) the test compound together with the reference agonist (1 nM) (all final concentrations). After 18 h, total RNA was extracted using TRIzol® Reagent (Invitrogen Life Technologies) and converted to cDNA using Transcriptor First Strand cDNA synthesis Kit (Roche Diagnostics GmbH) following manufacturer's instructions. cDNA was used as a template in RT-qPCR, which was carried out using Mx3000P Real-Time PCR System (Stratagene), FastStart SYBR Green Master Mix (Roche) and specific primers for AR target genes, PSA, TMPRSS2 and FKBP51. Analyzed GAPDH mRNA levels were used to normalize the amounts of total RNA between the samples. Fold changes (ligand inductions) were calculated using the formula $2^{-(\Delta\Delta Ct)}$, where $\Delta\Delta Ct$ is $\Delta Ct_{(ligand)} - \Delta Ct_{(EtOH-DMSO)}$, $\Delta Ct$ was $Ct_{(gene\ x)} - Ct_{(GAPDH)}$ and Ct was the cycle at which the threshold was crossed. Gene expression data were expressed as relative mRNA level (mRNA level of the gene of interest divided by mRNA level of GAPDH) of each gene for a given compound. The compounds of the present invention efficiently silenced AR target gene expression in VCaP cells.

LNCaP Proliferation Assay

The ability of the compounds of the present invention to inhibit prostate cancer cell growth was studied in androgen sensitive human prostate adenocarcinoma cell line, LNCaP. The LNCaP cells may be also genetically modified to over-express AR, thus mimicking CRPC. The cells were seeded onto 96-well plates (5000 cells/well) and cultured for 24 h. The six replicate wells were treated either with (i) vehicle (DMSO) or (ii) 0.1 nM R1881 (reference agonist, Perkin-Elmer), or (iii) increasing concentrations of BIC (the reference antagonist), or (iv) the test compound together with the reference agonist (0.1 nM) (all final concentrations) for 5 days. LNCaP cell proliferation was measured on day 0, day 1, day 3 and day 5 using Promega's Cell Titer 96® AQ$_{ueous}$ One Solution Cell Proliferation Assay kit according to manufacturer's instructions. 20 µl of the Cell Titer reagent was added into 100 µl of cell culture medium in each well and the cells were allowed to grow for one hour in the incubator. The culture medium was transferred into the wells of the measuring plate and the absorbance at 492 nm was recorded. The compounds of the present invention inhibited LNCaP proliferation.

The compounds of the present invention exhibit little or no agonistic activity to androgen receptor. Because these compounds are potent AR antagonists they can be used not only to treat prostate cancer but to treat other androgen receptor related conditions and diseases such as benign prostate hyperplasia, hair loss, acne, hirsutism, male hypersexuality or polycystic ovarian syndrome.

The compound of the present invention may be used alone or in combination i.e. administered simultaneously, separately, or sequentially, with other active agents.

As it pertains to the treatment of cancer, the compounds of this invention are most preferably used alone or in combination with anti-androgenic cancer treatments. Such compounds may also be combined with agents which suppress the production of circulating testosterone such as LHRH agonists or antagonists or with surgical castration.

The present invention also contemplates use of an anti-estrogen and/or aromatase inhibitor in combination with a compound of the present invention, for example, to assist in mitigating side effects associated with anti-androgen therapy such as gynecomastia.

AR belongs to the superfamily of nuclear receptors and the compounds of the present invention can also be used as scaffolds for drug design for other nuclear hormone receptors such as estrogen receptor or peroxisome proliferatoractivated receptor. Therefore, the compounds of the present invention can also be further optimized to be used in treating other conditions and diseases such as ovarian cancer, breast cancer, diabetes, cardiac diseases, metabolism related diseases of the periphery and central nervous system in which nuclear receptors play a role.

The compounds of the invention may be administered by intravenous injection, by injection into tissue, intraperitoneally, orally, or nasally. The composition may have a form selected from the group consisting of a solution, dispersion, suspension, powder, capsule, tablet, pill, controlled release capsule, controlled release tablet, and controlled release pill.

The invention claimed is:

1. A compound having formula (I)

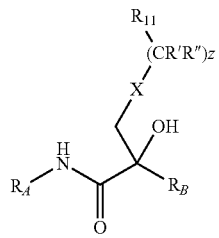

(I)

or an N-oxide, stereoisomer, or a pharmaceutically acceptable salt thereof;

where

R' and R" are each independently selected from the group consisting of H and alkyl;

z is an integer 0 to 3;

X is selected from the group consisting of O, S, S(O), $SO_2$, NR12, where R12 is selected from the group consisting of H, alkyl and COR, where R is hydrogen or alkyl; $CH_2$ and CO; or when z is 0, then X may be N and forms together with R11 a heterocyclic ring selected from the group consisting of morpholine, 1,2,4-triazole, imidazole and N-substituted imidazole; and R11, when not forming a ring with X as defined above, is selected from the group consisting of alkyl, alkenyl, (per)haloalkyl, haloalkenyl, alkyl-CN and an aryl, heteroaryl, aliphatic or heteroaliphatic, 3-7-membered ring optionally substituted with 1-5 substituents selected from the group consisting of alkyl, alkoxy, hydroxyl, halogen, (per)haloalkyl, CN, $NO_2$, COR, COOR, CONHR, $NR_2$, $NHCOCF_3$, NHCOR, NHCONHR, NHCOOR, OCONHR, $NHSO_2R$, $NHCSCH_3$, SR, SOR and $SO_2R$, where R is as defined above;

$R_B$ is a heteroaromatic ring having 6 ring members and being optionally substituted at one or more ring carbon atoms, of which ring members 1 or 2 are N atoms and the other ring members are carbon atoms, or $R_B$ is an optionally substituted phenyl group, the substituent(s) in $R_B$ being selected from the group consisting of alkyl, alkoxy, hydroxy, halogen, (per)haloalkyl, CN, $NO_2$, COR, COOR, $NR_2$, $NHCOCF_3$, NHCOR, NHCONHR, NHCOOR, OCONHR, CONHR, where R is as defined above; $NHCSCH_3$, SR, SOR and $SO_2R$, where R is as defined above, or, when $R_B$ is an optionally substituted phenyl group, then two adjacent substituents may also form with the carbon atoms, to which they are attached, a substituted or unsubstituted aliphatic, heteroaliphatic or heteroaromatic, ring; and $R_A$ is a mono- or bicyclic heteroaromatic ring system having 6 to 10 ring members and being optionally substituted at one or more ring carbon atoms, of which ring members 1 to 4 are N atoms and the other ring members are carbon atoms, whereby when $R_B$ is an optionally substituted phenyl group, then the ring attached to the NH group contains at least one N atom as a ring member, or when $R_B$ is an optionally substituted heteroaromatic ring, then $R_A$ may also be an optionally substituted phenyl group, the substituent(s) in $R_A$ being selected from the group consisting of alkyl, alkoxy, halogen, (per)haloalkyl, hydroxy, $(CH_2)_n CHO$, where n is an integer 0-6; CN, $NO_2$, COR, COOR and CONHR, where R is as defined above, or when $R_A$ is an optionally substituted phenyl group, then two adjacent substituents may also form with the carbon atoms, to which they are attached, a substituted or unsubstituted aliphatic, heteroaliphatic or heteroaromatic ring.

2. A compound according to claim 1, where $R_B$ is selected from the group consisting of:

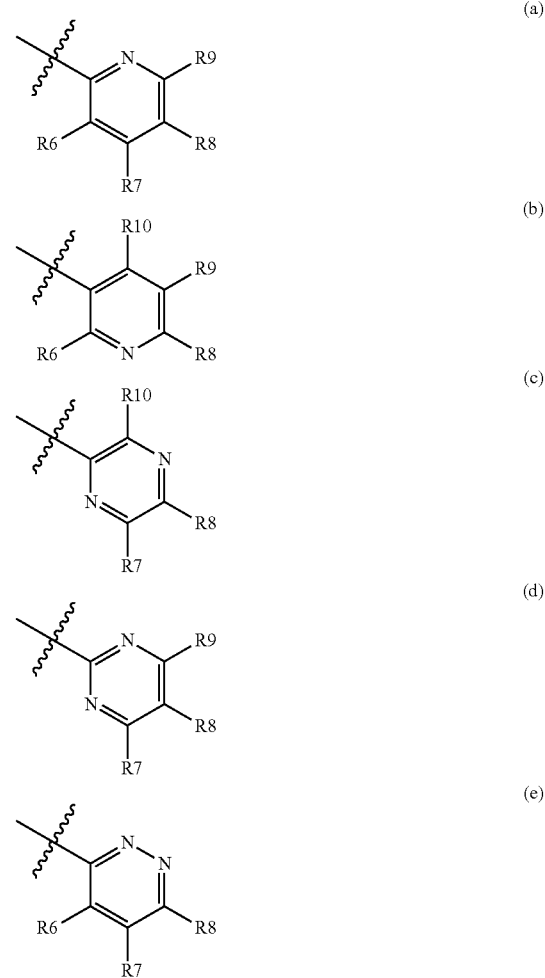

-continued

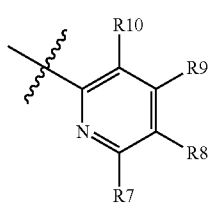
(f)

where R6-R10 are selected from the group consisting of hydrogen, alkoxy, alkyl, hydroxy, halogen, (per)haloalkyl, CN, NO₂, COR, COOR, NR₂, NHCOCF₃, NHCOR, NHCONHR, NHCOOR, OCONHR, CONHR, where R is hydrogen or alkyl; NHCSCH₃, SR, SOR and SO₂R.

3. A compound according to claim 1, where R$_B$ is an optionally substituted phenyl group of formula

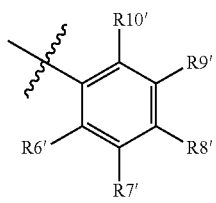
(g)

where R6'-R10' are selected from the group consisting of hydrogen, alkyl, alkoxy, hydroxyl, halogen, (per)haloalkyl, CN, NO₂, COR, COOR, NR₂, NHCOCF₃, NHCOR, NHCONHR, NHCOOR, OCONHR, CONHR, where R is hydrogen or alkyl; NHCSCH₃, SR, SOR and SO₂R, where R is hydrogen or alkyl, or two adjacent substituents may also form with the carbon atoms, to which they are attached, a substituted or unsubstituted aliphatic, heteroaliphatic or heteroaromatic ring.

4. A compound according to claim 2, where R$_A$ is selected from the group consisting of:

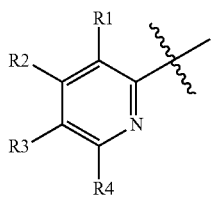
(h)

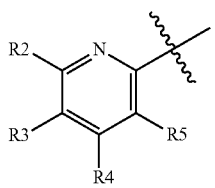
(i)

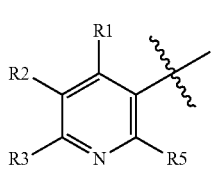
(j)

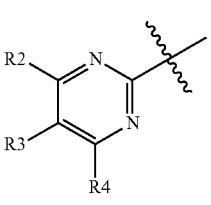
(k)

(l)

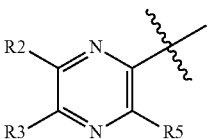

(m)

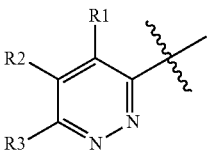

(n)

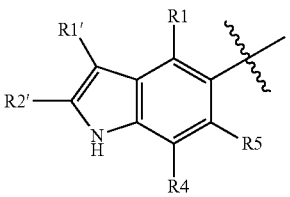

(o)

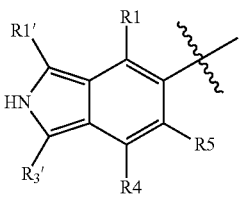

(p)

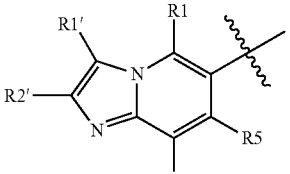

(q)

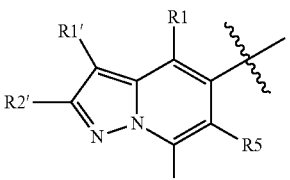

(r)

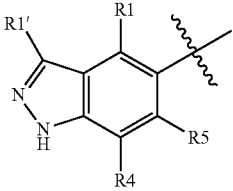

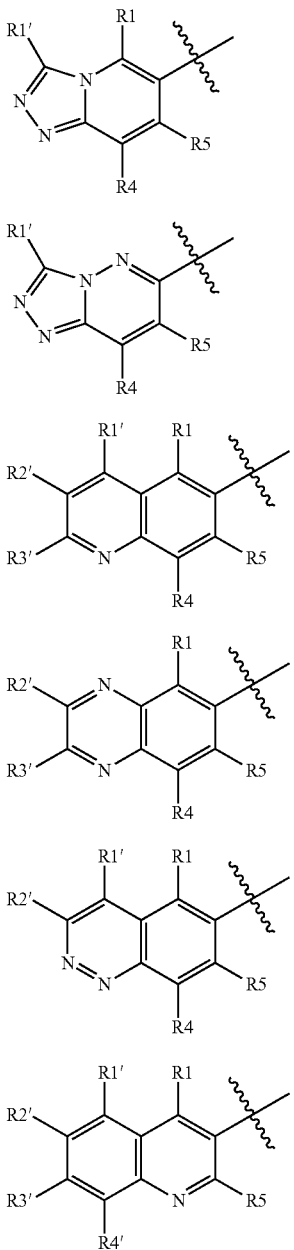

where R1 to R5 and R1' to R4' are selected from hydrogen, alkyl, alkoxy, hydroxy, halogen, (per)haloalkyl, (CH$_2$)$_n$CHO, where n is an integer 0-6; CN, NO$_2$, COR, COOR and CONHR, where R is hydrogen or alkyl.

5. A compound according to claim 2, where R$_A$ is an optionally substituted phenyl group of formula

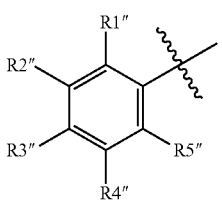

where R1"-R5" are selected from the group consisting of hydrogen, alkyl, alkoxy, hydroxy, halogen, (per)haloalkyl, hydroxy, (CH$_2$)$_n$CHO, where n is an integer 0-6; CN, NO$_2$, COR, COOR and CONHR, where R is hydrogen or alkyl, or two adjacent substituents may also form with the carbon atoms, to which they are attached, a substituted or unsubstituted aliphatic, heteroaliphatic or heteroaromatic ring.

6. A compound according to claim 1, where the compound has the formula

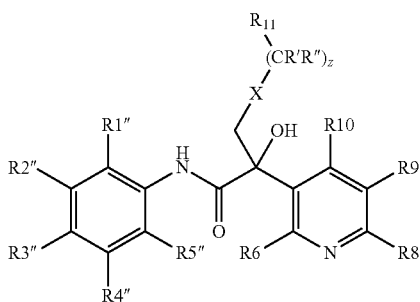

where R1"-R5" are selected from the group consisting of hydrogen, alkyl, alkoxy, hydroxy, halogen, (per)haloalkyl, hydroxy, (CH$_2$)$_n$CHO, where n is an integer 0-6; CN, NO$_2$, COR, COOR and CONHR, where R is hydrogen or alkyl, or two adjacent substituents may also form with the carbon atoms, to which they are attached, a substituted or unsubstituted aliphatic, heteroaliphatic or heteroaromatic ring, R6, R8, R9, and R10 are selected from the group consisting of hydrogen, alkoxy, alkyl, hydroxy, halogen, (per)haloalkyl, CN, NO$_2$, COR, COOR, NR$_2$, NHCOCF$_3$, NHCOR, NHCONHR, NHCOOR, OCONHR, CONHR, where R is hydrogen or alkyl; NHCSCH$_3$, SR, SOR and SO$_2$R, and R11, R', R", X and z are as defined in claim 1; or a pharmaceutically acceptable salt thereof.

7. A compound according to claim 6, where R1", R4", R5", R6 and R10 are hydrogen; R2" is trifluoromethyl or halo; R3" is cyano; R8 is CF$_3$ or halo; R9 is hydrogen or halo; z is 0 or 1 (R'=R"=H); X is SO$_2$; and R11 is cycloalkyl, alkyl selected from the group consisting of methyl, ethyl, tert-butyl, isopropyl, and isopentyl, or phenyl or pyridinyl optionally substituted with halo.

8. A compound according to claim 1, where the compound has the formula

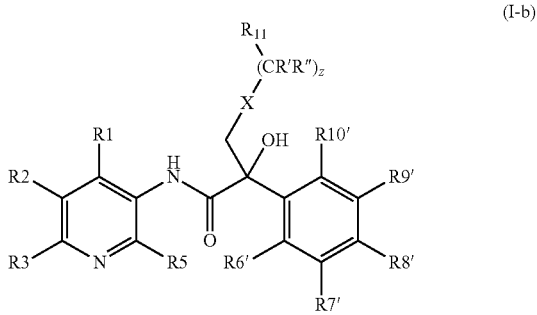

wherein R1, R2, R3, and R5 are selected from hydrogen, alkyl, alkoxy, hydroxy, halogen, (per)haloalkyl, (CH$_2$)$_n$CHO, where n is an integer 0-6; CN, NO$_2$, COR, COOR and CONHR, where R is hydrogen or alkyl, R6'-R10' are selected from the group consisting of hydrogen, alkyl, alkoxy, hydroxyl, halogen, (per)haloalkyl, CN, NO₂, COR, COOR, NR₂, NHCOCF₃, NHCOR, NHCONHR, NHCOOR, OCONHR, CONHR, where R is hydrogen or alkyl; NHCSCH₃, SR, SOR and SO₂R, where R is hydrogen or alkyl, or two adjacent substituents may also form with the carbon atoms, to which they are attached, a substituted or unsubstituted aliphatic, heteroaliphatic or heteroaromatic ring, and R11, R', R", X and z are as defined in claim 1;
or a pharmaceutically acceptable salt thereof.

9. A compound according to claim 8, where R1, R5, R6', R7' and R10' are hydrogen; R2 is trifluoromethyl or halo; R3 is cyano; R8' is halo; R9' is hydrogen or halo; z is 0; X is SO₂; and R11 is cyclopropyl or alkyl, selected from the group consisting of methyl, ethyl, tert-butyl, isopropyl, and isopentyl.

10. A compound according to claim 1, where the compound has the formula

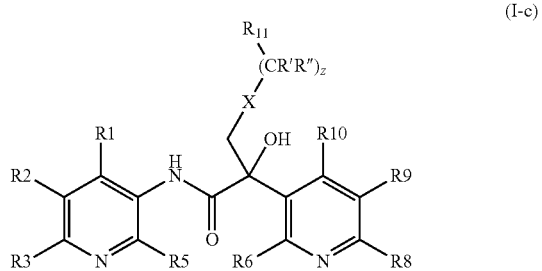

(I-c)

where R1, R2, R3, and R5 are selected from hydrogen, alkyl, alkoxy, hydroxy, halogen, (per)haloalkyl, (CH₂)ₙ CHO, where n is an integer 0-6; CN, NO₂, COR, COOR and CONHR, where R is hydrogen or alkyl, R6, R8, R9 and R10 are selected from the group consisting of hydrogen, alkoxy, alkyl, hydroxy, halogen, (per) haloalkyl, CN, NO₂, COR, COOR, NR₂, NHCOCF₃, NHCOR, NHCONHR, NHCOOR, OCONHR, CONHR, where R is hydrogen or alkyl; NHCSCH₃, SR, SOR and SO₂R, and R11, R', R", X and z are as defined in claim 1;
or a pharmaceutically acceptable salt thereof.

11. A compound according to claim 10, where R1, R5, R6, R7 and R10 are hydrogen; R2 is trifluoromethyl or halo; R3 is cyano; R8 is halo; R9 is hydrogen or halo; z is 0; X is SO₂; and R11 is isopropyl.

12. The compound according to claim 1, wherein said N-oxide is a pyridine N-oxide.

13. A compound according to claim 1, where the compound is selected from the group consisting of:
2-(6-chloropyridin-3-yl)-N-[4-cyano-3-(trifluoromethyl) phenyl]-3-(ethanesulfonyl)-2-hydroxypropanamide;
2-cyano-5-[3-(ethylsulfonyl)-2-(4-fluorophenyl)-2-hydroxypropanamido]-3-(trifluoromethyl)pyridine-1-oxide;
N-[6-cyano-5-(trifluoromethyl)pyridin-3-yl]-3-(ethanesulfonyl)-2-(4-fluorophenyl)-2-hydroxypropanamide;
5-[2-(4-chlorophenyl)-3-(ethylsulfonyl)-2-hydroxypropanamido]-2-cyano-3-(trifluoromethyl)pyridine-1-oxide;
2-(4-chlorophenyl)-N-[6-cyano-5-(trifluoromethyl)pyridin-3-yl]-3-(ethanesulfonyl)-2-hydroxypropanamide;
2-(6-chloropyridin-3-yl)-N-[4-cyano-3-(trifluoromethyl) phenyl]-2-hydroxy-3-[(3-methylbutane)sulfonyl]propanamide;
2-(3,4-difluorophenyl)-3-(ethanesulfonyl)-2-hydroxy-N-[3-(trifluoromethyl)-[1,2,4]triazolo[4,3-b]pyridazin-6-yl]propanamide;
N-(3-chloro-4-cyanophenyl)-3-{[(4-chlorophenyl)methane]sulfonyl}-2-(6-chloropyridin-3-yl)-2-hydroxypropanamide;
N-(3-chloro-4-cyanophenyl)-3-[(4-chlorobenzene)sulfonyl]-2-(6-chloropyridin-3-yl)-2-hydroxypropanamide;
3-(ethanesulfonyl)-2-(4-fluorophenyl)-2-hydroxy-N-[3-(trifluoromethyl)-[1,2,4]triazolo[4,3-b]pyridazin-6-yl] propanamide;
2-(4-chlorophenyl)-3-(ethanesulfonyl)-2-hydroxy-N-[3-(trifluoromethyl)-[1,2,4]triazolo[4,3-b]pyridazin-6-yl] propanamide;
2-(6-chloropyridin-3-yl)-N-[4-cyano-3-(trifluoromethyl) phenyl]-2-hydroxy-3-(propane-2-sulfonyl)propanamide;
2-(6-chloropyridin-3-yl)-N-[6-cyano-5-(trifluoromethyl) pyridin-3-yl]-2-hydroxy-3-(propane-2-sulfonyl)propanamide;
2-chloro-5-(1-((3-chloro-4-cyanophenyl)amino)-3-(4-chlorophenyl)sulfonyl)-2-hydroxy-1-oxopropan-2-yl) pyridine 1-oxide;
N-(3-chloro-4-cyanophenyl)-3-(4-fluorobenzenesulfonyl)-2-hydroxy-2-[6-(trifluoromethyl)pyridin-3-yl] propanamide;
N-(3-chloro-4-cyanophenyl)-2-(6-chloropyridin-3-yl)-3-[(6-chloropyridin-3-yl)sulfonyl]-2-hydroxypropanamide;
2-(6-chloropyridin-3-yl)-N-[4-cyano-3-(trifluoromethyl) phenyl]-2-hydroxy-3-(2-methylpropane-2-sulfonyl) propanamide;
2-(6-chloropyridin-3-yl)-N-[4-cyano-3-(trifluoromethyl) phenyl]-3-(cyclopropanesulfonyl)-2-hydroxypropanamide;
2-(6-chloropyridin-3-yl)-N-[4-cyano-3-(trifluoromethyl) phenyl]-2-hydroxy-3-methanesulfonylpropanamide;
5-{3-(tert-butylsulfonyl)-1-[(4-cyano-3-(trifluoromethyl) phenyl)amino]-2-hydroxy-1-oxopropan-2-yl}-2-chloropyridine 1-oxide;
or a pharmaceutically acceptable salt thereof.

14. A pharmaceutical composition comprising an effective amount of one or more compounds or pharmaceutically acceptable salts thereof according to claim 1 together with a suitable carrier and conventional excipients.

15. A process for preparing a compound of formula (I) as defined in claim 1, where X is O, SO or SO₂, comprising an epoxy compound of formula (5),

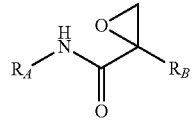

5 where R_A and R_B are as defined above, with a compound of formula (II),

R11-(CR'R")_z—X'H       (II)

where R11, R', R" and z are as defined above and X' is O or S, to obtain a compound of formula (I), where X is O or S, and, if desired, oxidizing the obtained compound where X is S to obtain a compound of formula (I), where X is SO or SO₂.

16. The process according to claim 15, where the process is carried out via the following reaction steps:

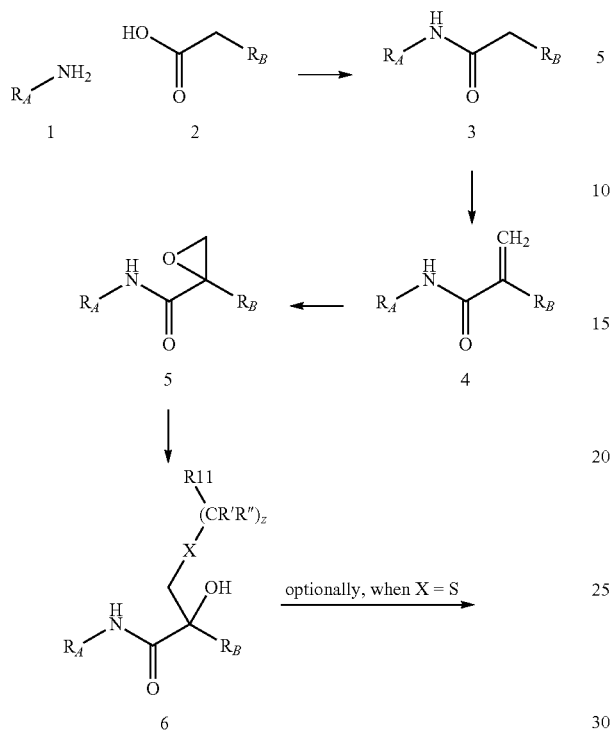

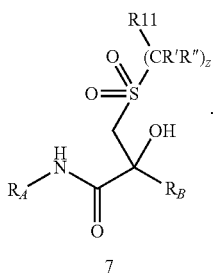

17. A method of treating androgen receptor related disorders in a patient in need thereof comprising administering to said patient a therapeutically effective amount of the compound according to claim 1 or pharmaceutically acceptable salt thereof.

18. The method according to claim 17 wherein the disorder is benign prostate hyperplasia.

19. The method according to claim 17 wherein the disorder is prostate cancer.

20. The method according to claim 19 wherein the prostate cancer is castration-resistant prostate cancer.

21. The method according to claim 17 wherein said compound or pharmaceutically acceptable salt thereof is administered simultaneously, separately or sequentially with another active agent.

* * * * *